(12) United States Patent
Pagani et al.

(10) Patent No.: US 9,097,637 B2
(45) Date of Patent: Aug. 4, 2015

(54) INTEGRATED ELECTRONIC DEVICE FOR MONITORING PARAMETERS WITHIN A SOLID STRUCTURE AND MONITORING SYSTEM USING SUCH A DEVICE

(75) Inventors: Alberto Pagani, Nova Milanese (IT); Bruno Murari, Monza (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 127 days.

(21) Appl. No.: 13/996,259

(22) PCT Filed: Oct. 20, 2011

(86) PCT No.: PCT/EP2011/068359
§ 371 (c)(1),
(2), (4) Date: Sep. 9, 2013

(87) PCT Pub. No.: WO2012/084295
PCT Pub. Date: Jun. 28, 2012

(65) Prior Publication Data
US 2013/0342186 A1 Dec. 26, 2013

(30) Foreign Application Priority Data
Dec. 22, 2010 (IT) ................. MI2010A2365

(51) Int. Cl.
*G01N 27/00* (2006.01)
*G01M 5/00* (2006.01)
*G01L 1/26* (2006.01)

(52) U.S. Cl.
CPC *G01N 27/00* (2013.01); *G01L 1/26* (2013.01); *G01M 5/0083* (2013.01)

(58) Field of Classification Search
CPC ........ G01L 1/26; G01M 5/0083; G01N 27/00
USPC ........................................ 324/71.1
See application file for complete search history.

(56) References Cited

U.S. PATENT DOCUMENTS

| 5,281,836 A | * | 1/1994 | Mosser et al. ................ 257/254 |
| 6,950,767 B2 | | 9/2005 | Yamashita et al. |
| 7,038,470 B1 | * | 5/2006 | Johnson ....................... 324/664 |

(Continued)

FOREIGN PATENT DOCUMENTS

| EP | 0886144 A1 | 12/1998 |
| WO | 0013438 A1 | 3/2000 |

(Continued)

*Primary Examiner* — Hoai-An D Nguyen
(74) *Attorney, Agent, or Firm* — Allen, Dyer, Doppelt, Milbrath & Gilchrist, P.A.

(57) ABSTRACT

An electronic device is for detecting and monitoring a local parameter within a solid structure. The electronic device may include an integrated detection module having a functional IC including an integrated sensor to detect the local parameter within the solid structure, and an antenna and having a functional circuitry surface facing towards an outside of the functional IC, and a passivation layer to cover at least the functional circuitry surface of the functional IC so that the functional IC is hermetically sealed and galvanically insulated from a surrounding environment. The electronic device may also include an RF circuit to be coupled with the integrated detection module and having a remote antenna configured to transmit/receive signals for telecommunications and energy exchange with the antenna. The antenna, the RF circuit, and the remote antenna may wirelessly communicate via an electromagnetic coupling.

27 Claims, 6 Drawing Sheets

(56) References Cited

U.S. PATENT DOCUMENTS

| | | | |
|---|---|---|---|
| 7,363,800 B2* | 4/2008 | Gysling | 73/19.01 |
| 7,551,058 B1* | 6/2009 | Johnson et al. | 340/10.41 |
| 2009/0033467 A1 | 2/2009 | Finocchiaro et al. | |
| 2011/0115613 A1* | 5/2011 | Kaga et al. | 340/10.51 |
| 2013/0247678 A1* | 9/2013 | Manohara et al. | 73/753 |

FOREIGN PATENT DOCUMENTS

| | | |
|---|---|---|
| WO | 2007036922 A1 | 4/2007 |
| WO | 2009053757 A2 | 4/2009 |

* cited by examiner

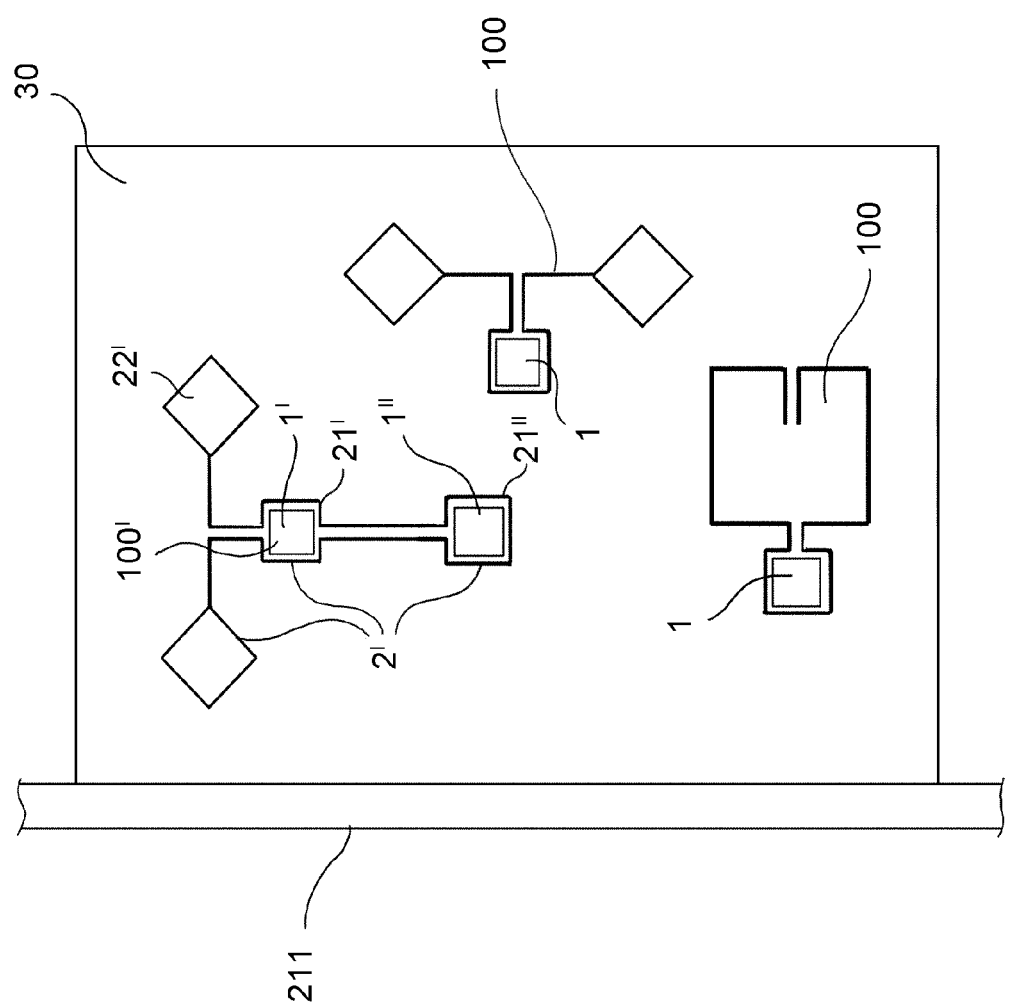

# INTEGRATED ELECTRONIC DEVICE FOR MONITORING PARAMETERS WITHIN A SOLID STRUCTURE AND MONITORING SYSTEM USING SUCH A DEVICE

TECHNICAL FIELD

The present disclosure relates to electronic devices for monitoring parameters within a solid structure, and in particular, to a device and related method for detecting and monitoring parameters.

BACKGROUND

In solid structures, particularly in load-bearing structures of, for example, bridges, buildings, tunnels, railways, containment walls, dams, embankments, pipelines and underground structures of metropolitan transport lines, and so on, it is very important to monitor, in many points, significant parameters, like, for example, pressure, temperature and mechanical stresses. Such monitoring is carried out periodically or continuously, and is useful both at the initial stage and during the lifetime of the structure.

For this purpose, an approach in this field includes application of electronic monitoring devices based on electronic sensors, capable of providing good performance at low cost. Usually, such devices are applied onto the surface of the structures to be monitored, or inside recesses already foreseen in the structure and accessible from the outside.

Such devices are not however able to exhaustively detect the parameters within the structure to be monitored, which it may be useful to know in order to evaluate the quality of the structure, its safety, its ageing, its reaction to variable atmospheric conditions, and so on. Moreover, such devices can only be applied after the structure has been built, and not while it is being built. Therefore, they are unable to evaluate possible initial defects.

An approach to these requirements disclosed in U.S. Pat. No. 6,950,767 to Yamashita et al., which provides an electronic monitoring device entirely contained, i.e. "buried", within the material (for example, reinforced concrete) from which the structure to be monitored is made. More specifically, the device buried in the structure is an entire system encapsulated in a single container, made up of different parts, assembled on a substrate, such as integrated circuits, sensors, antenna, capacitors, batteries, memories, control units, and yet more, made in different chips connected together through electrical connections made with metallic connections. This approach is of the type System-in-Package (SiP), in which the SiP is coated with a casing of mold material, such as an epoxy resin. Such a system communicates with the outside by way a radio communication sub-system contained therein, which must have an antenna sized in such a way to be able to communicate with a remote system.

The system of U.S. Pat. No. 6,950,767 to Yamashita et al. also comprises sub-systems having functions correlated with the power supply, for example, rectifiers in the case in which it receives energy from the outside, through electromagnetic waves, or else its own battery for generating the power supply internally. It should be observed that a monitoring system intended to be "embedded" initially in a building material (for example, liquid concrete, which will then solidify) and to then remain "buried" in the solid structure, is subjected to critical conditions, for example, extremely high pressures, which can even be a few hundreds of atmospheres. There are also numerous other causes of wearing, over time, due, for example, to water infiltration, capable of damaging the system.

A potential drawback to systems, such as that in U.S. Pat. No. 6,950,767 to Yamashita et al., derives from the fact that they are complex systems, even though they are enclosed in a package, and can therefore be damaged when facing the operating conditions in which they must work. In particular, the electrical interconnections between the various parts of the SiP can be vulnerable, faced with the mechanical stress that the SiP inserted in the structure must withstand.

Moreover, the "window" that must be left in the package to allow the sensor to detect the relative parameter can be a weak point for possible infiltrations of humidity. Furthermore, a crack or imperfection in the coating material can allow water to penetrate inside the SiP and cause short-circuits. In addition to water, other substances, such as potentially corrosive acids, can also infiltrate.

In general, although designed for the mentioned use, the reliability of systems like that of U.S. Pat. No. 6,950,767 to Yamashita et al. has a limitation due to the complexity of the structure of such systems, although miniaturized. It should also be observed that this approach may provide the use of numerous SiPs in different points of the structure to be monitored, but in positions that are not known. The positions must be estimated based on techniques like trilateration. This can cause various drawbacks, including: if the estimation of the position of the sensors is incorrect, the data obtained by the external remote data collection and processing system can be inaccurate or difficult to interpret; and if the structure is made from reinforced concrete, and comprises metallic structures (for example, steel rods), it is impossible to control and avoid electromagnetic shield effects, and this can jeopardize the communication with the outside and/or the detection of the position of the different SiPs.

SUMMARY

An electronic device is for detecting and monitoring a local parameter within a solid structure. The electronic device may include an integrated detection module having a functional IC including an integrated sensor configured to detect the local parameter within the solid structure, and an antenna and having a functional circuitry surface facing towards an outside of the functional IC, and a passivation layer configured to cover at least the functional circuitry surface of the functional IC so that the functional IC is hermetically sealed and galvanically insulated from a surrounding environment. The electronic device may also include an RF circuit to be coupled with the integrated detection module and having a remote antenna configured to transmit/receive signals for telecommunications and energy exchange with the antenna. The antenna, the RF circuit, and the remote antenna may be configured to wirelessly communicate via an electromagnetic coupling.

BRIEF DESCRIPTION OF THE DRAWINGS

Further characteristics and advantages of the electronic device for monitoring parameters according to the disclosure shall become clear from the following description of preferred example embodiments, given for indicating and not limiting purposes, with reference to the attached figures, in which:

FIG. 7 is another detailed diagram showing another embodiment of an internal monitoring sub-system, according to the present disclosure.

DETAILED DESCRIPTION

An aspect of the present disclosure is directed to an integrated electronic device for monitoring parameters within a solid structure, which is improved so as to at least partially avoid the drawbacks described above with reference to the prior art. In particular, an improved monitoring device is proposed that is simple, robust and more reliable, and allows at least one physical quantity of the solid structure to be measured, in the more general context of improving the safety of architectural structures of various types.

Figure 1:
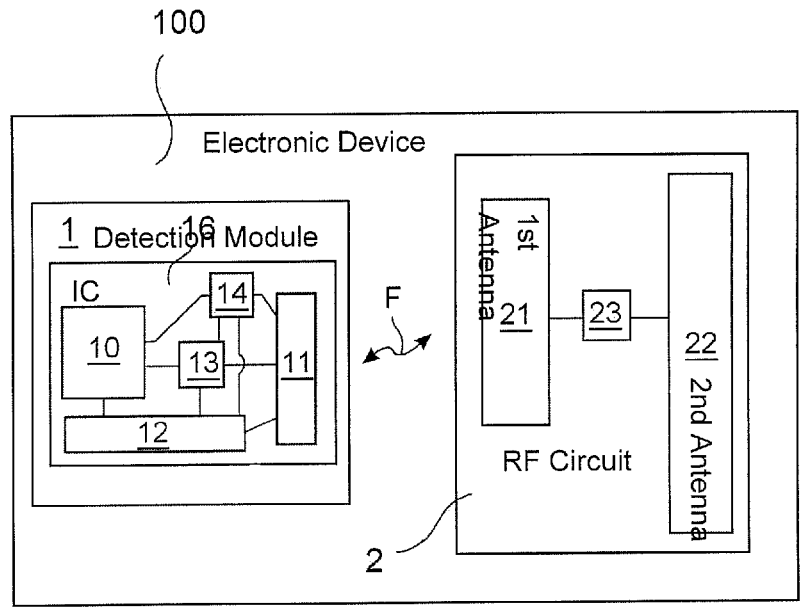
FIG. 1 is a schematic diagram of an electronic monitoring device, according to an embodiment of the present disclosure.

With reference to FIG. 1, an electronic device 100 for detecting and monitoring one or more local parameters within a solid structure is described (which henceforth will be defined as "monitoring device" for the sake of brevity), according to an example of the present disclosure. The monitoring device 100 comprises an integrated detection module 1, made on a single semiconductor chip (henceforth defined simply as chip), wherein the semiconductor is, typically, silicon. The monitoring device 100 also comprises, connected to the integrated detection module 1, electromagnetic means or an electromagnetic circuit (i.e. an RF circuit) 2 for transmitting/receiving telecommunications signals and exchanging energy between the integrated detection module 1 and an external control and data collection system, not shown in FIG. 1.

The integrated detection module 1 comprises an integrated functional circuitry portion or functional integrated circuit (IC) 16. For the purposes of the present description, by the term "functional IC," it is meant to indicate the portion of the integrated detection module 1 arranged to implement the functional blocks comprised in the module itself, such as, for example, those described hereafter.

As illustrated in FIG. 1, the functional IC 16 of the integrated detection module 1 comprises an integrated sensor 10 capable of detecting and monitoring one or more parameters, characteristic of the structure to be monitored, which parameters are to be kept under control. Typically, such parameters are a pressure and/or a temperature and/or a mechanical stress.

It should be observed that, according to alternative embodiments, there can be more than one sensor integrated in the integrated detection module 1, and each of them can detect one or more parameters, as will be shown more clearly hereafter. It should also be noted that the detectable parameters can be different from those quoted above as examples, provided that they cause a detectable effect on the semiconductor or on structures integrated in the single chip from which the integrated detection module 1 is made.

Typically, the integrated sensor 10 is able to transform a temperature or pressure value into an electrical variable, for example, exploiting the known variations that such parameters induce on the mobility of electrons/holes in the semiconductor. Regarding this, it is known that mobility depends on temperature, independently from the crystalline orientation of the semiconductor material, and on pressure, in a manner dependant on the crystalline orientation of the semiconductor material, according to the laws that regulate the phenomenon of piezoresistance. In particular, with reference to the Miller indices, using common notations when defining planes and axes characterizing a crystal, consider, for example, a crystal of type N in the plane (001). In such an example, the sensitivity to mechanical stress, therefore to pressure, is at its maximum if such a stress is applied along axes [100] and [010] with respect to a reference system associated with the crystalline orientation, whereas it is at its minimum along axes [110]. Therefore, with suitable configurations of components integrated on the chip of the integrated detection module 1, it is possible to build pressure sensors, by compensating for the dependency from temperature, or vice-versa temperature sensors, by compensating for the dependency from pressure. It should be noted that other dependencies upon ageing and wear are easily discriminated from the previous ones and compensated, taking into account that they emerge over very long time periods, for example, years.

According to an embodiment, the sensor 10 is a pressure sensor formed with four resistors integrated in Wheatstone bridge configuration, in which two pressure-sensitive resistors are oriented along the axes [100] and [010] associated with the crystalline orientation, whereas the other two are oriented along the axes [110], which is an orientation coinciding with the angle of the minimum sensitivity axis of the piezoresistive effect. In this way, the dependence of the measurement on the "temperature" parameter is totally negligible and, in this sense, it can be said that the "pressure" parameter is measured in a way substantially independent from the "temperature" parameter.

According to a further example embodiment, the sensor 10 is a pressure and temperature sensor made by a first and second ring oscillator, each comprising a plurality of integrated components (for example, three or an odd number of "inverters", or else two or an even number of "differential buffers") in cascade. The integrated components of the first oscillator include semiconductor material with different crystalline orientation from the orientation of the material of the second oscillator: for example, respectively, with orientation along the axis [110] and [100] or [010].

In this way, the oscillation frequency of the first oscillator with orientation along [110], in which the piezoelectric (i.e., piezoresistive) effect is at its minimum, substantially depends on the temperature only, since the effect of the pressure is completely negligible; therefore, such a frequency can be interpreted as the output of a temperature sensor. The oscillation frequency of the second oscillator with orientation [100] or [010], if cleared of the effect of temperature, which is known thanks to the output of the first oscillator, depends substantially on the pressure only; therefore, such a frequency can be interpreted as the output of a pressure sensor. It should be noted that, in the example embodiments described above, in order for the sensor 10 to work, it is not necessary for there to be membranes or other components outside of the integrated detection module 1.

Again with reference to FIG. 1, it should be observed that the functional IC 16 of the integrated detection module 1 also comprises an integrated antenna 11. The integrated antenna 11 performs the function of wirelessly transmitting the measured data (i.e., the intensity of each of the electric variables dependent on and representative of, respectively, one of the physical quantities to be detected and monitored) to the outside of the integrated detection module 1. The integrated antenna 11 also performs the function of receiving operating commands from the outside.

Furthermore, the integrated antenna 11 performs the additional function of receiving radio frequency waves necessary for remote power supplying of the integrated module 1, without the need for batteries or power supply in loco. The integrated antenna 11 is made by way of at least one metallization layer, for example, aluminum or copper, in the integrated detection module 1.

As illustrated again in FIG. 1, the functional IC 16 of the integrated detection module 1 also comprises the following auxiliary functional blocks: a power supply circuit 12, a driving circuit 13, and a control circuit 14. The power supply circuit 12 is arranged to obtain the electrical power supply necessary for the operation of the integrated detection module 1 from radio frequency waves received by the integrated antenna 11. For this purpose, the power supply circuit 12 is connected to the integrated antenna 11 to receive radio frequency waves and it is also connected to the integrated sensor 10 and to the other functional blocks of the integrated functional circuitry 16, i.e., functional IC 16 (in the example of FIG. 1, the driving circuit 13 and the control circuit 14) to supply electrical power.

The driving circuit 13 is arranged to drive the integrated antenna 11 so that it wirelessly transmits the measured data. For this purpose, the driving circuit 13 is operatively connected to the integrated antenna 11, and also to the sensor 10, from which it receives the measured data, and to the control circuit 14, from which it receives the relative commands. The control circuit 14 is arranged to control the operation of the integrated functional circuitry present in the integrated module 1, according to what is dictated by operating commands sent from outside and received by the integrated antenna 11. For this purpose, the control circuit 14 is operatively connected on one side to the integrated antenna 11, through which it receives the operating commands, and on the other side to the sensor 10, to the driving circuit 13 and to the power supply circuit 12 to actuate such commands.

The power supply circuit 12, the driving circuit 13 and the control circuit 14 can be made by way of known circuits, for example, in the field of Radio Frequency Identifier (RFID) technology, or of Smart Card manufacturing technologies. Therefore, they will not be described here in detail. Regarding this, it should be noted that the operating mode of the integrated antenna 11 can be advantageously based on load modulation techniques, typical of RFID technology.

Figure 2A:
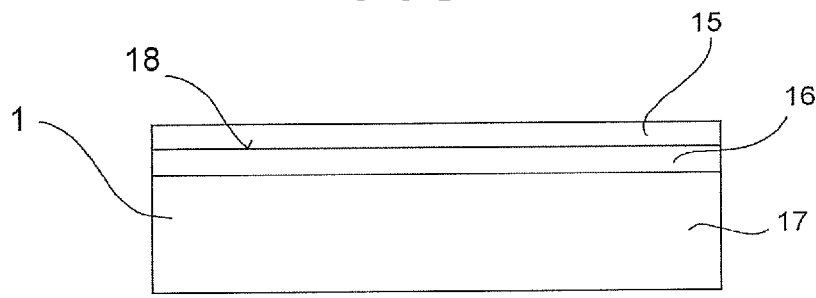
FIGS. 2A and 2B are two simplified section views respectively referring to two embodiments of an integrated detection module in the electronic monitoring device of FIG. 1.`
Figure 2B:
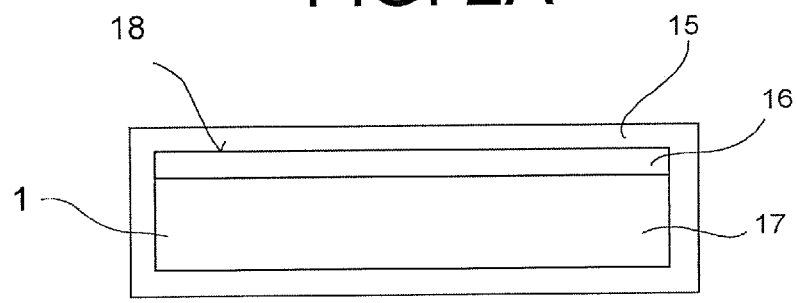

With reference to FIGS. 2A and 2B, some details of the physical structure of the integrated detection module 1 are discussed, the functional structure of which has been described above. The simplified section view of FIG. 2A represents a silicon substrate 17 and the functional IC 16. The functional IC 16 is schematically shown for the sake of simplicity by a single layer, but it can of course be made by a plurality of layers, as appreciated. It should be observed that the silicon substrate 17 and the functional IC 16 form the single chip on which the integrated detection module 1 is made.

The functional IC 16 comprises a functional surface 18 (i.e., a functional circuitry surface) facing towards the outside of such a chip. The functional surface 18 is therefore the part of the outer surface of the chip that belongs to the functional IC 16. The integrated detection module 1 also comprises a passivation layer 15.

In the embodiment shown in FIG. 2A, the passivation layer 15 is an impermeable and protective layer, arranged to completely cover at least said functional surface 18 of the functional IC 16, so that the integrated detection module 1, as a whole, is entirely hermetically sealed and galvanically insulated from the surrounding environment. Such a passivation layer 15 can be made, for example, from silicon oxide, silicon nitride or silicon carbide.

It should be observed that the passivation layer 15 is expressly made on the integrated detection module 1, and in particular, on the functional surface 18 of the functional IC 16, so that no metallization is accessible towards the outside. In particular, the passivation layer 15 advantageously also covers the possible metallizations, which are non-operative in the final application, metallizations that may be present on chips containing integrated circuits in order to allow their testing, before being cut from the silicon wafer on which they have been manufactured.

It should be noted that some parts of the integrated detection module 1, i.e. the "side" parts, in the section view of FIG. 2A, can be hermetically sealed by way of, for example, a seal ring, according to typical techniques, and therefore not shown in FIG. 2A. Moreover, the substrate 17 of the integrated detection module 1 (i.e. the "bottom" part in the section view of FIG. 2A) is sealed and galvanically insulated.

Therefore, the passivation layer 15 arranged to cover the functional surface 18 of the functional IC 16 (i.e. the "top" part of the chip, in the schematization of FIG. 2A) is on the one hand necessary, and on the other hand sufficient to ensure that the single chip of the integrated detection module 1 is, on the whole, hermetically sealed and galvanically insulated from the surrounding environment. It should be noted that such a seal and such complete galvanic insulation are made possible by the fact that all of the functions necessary for detecting the parameters to be monitored are performed by blocks present inside the single chip, in which the integrated detection module 1 is formed.

In particular, the integrated detection module 1, thanks to the characteristics described above, is advantageously capable of providing its functions without needing any wire and/or metallizations for the connections towards the outside of the integrated module itself. Therefore, it does not have any metallic terminal, i.e. no wire bonding and/or "pads" and/or "bumps", towards the outside, and therefore it can be entirely sealed and galvanically insulated.

Moreover, the integrated detection module 1 is able to perform its detection functions without needing further mediation blocks, and without needing further protective casings, against the solid material from which the structure to be monitored is made. It can therefore be embedded in such a structure, and placed in direct contact with it.

It should be observed that the absence of further protective casings does not make the integrated detection module 1 fragile, but rather improves its usability and reliability. Indeed, the passivation layer 15 makes the protection of the integrated detection module 1 complete with respect to water, humidity and any other external corrosion or degradation agent, without there being weak points, like, for example, metallizations, such as to be attacked by said agents.

Regarding this, it should be observed that such weak points could be attacked, where present, for example, in monitoring devices built as a system-in-package, also when there are protective casings around the entire SiP. Moreover, with regard to mechanical resistance, it is the semiconductor material itself, which forms the integrated detection module 1 and ensures the required performance.

Indeed, a semiconductor material like silicon has mechanical properties that allow it to resist, to not break, and to work correctly up to pressures of at least 1500 atmospheres, provided that such pressures are uniform, and such pressure values are still above the pressures inside the solid material in which the integrated detection module 1 is placed.

These characteristics allow the integrated detection module 1 to be embedded in the structure to be monitored during the building of the structure itself, for example, during a casting step of liquid concrete. They also allow the integrated module 1 to operate later, from inside the solid structure (for example, of reinforced concrete) after the concrete has solidified, having a long lifetime and good reliability parameters, with respect to typical requirements.

According to another embodiment of the integrated detection module 1, illustrated in FIG. 2B, the passivation layer 15 is made so as to completely coat the integrated module 1 after the silicon wafer on which it had been manufactured has been cut. Advantageously, such an embodiment provides a further guarantee of a hermetic seal and galvanic insulation of the integrated detection module 1, in the cases in which the approaches for protecting the parts other than the functional surface 18, already mentioned as known, are for whatever reason considered to be insufficient.

With reference again to FIG. 1, the electromagnetic circuit 2 for receiving/transmitting signals for telecommunications and energy exchange meets the requirement of allowing communication between the integrated detection module 1 and an external control and data collection system, situated remotely, for example, at a distance of a few centimeters or a few meters from the structure to be monitored and therefore from the integrated detection module 1. This implies the need to transmit near or far field electromagnetic energy, also taking into account the attenuations due to the solid structure to be monitored, which the electromagnetic fields must pass through.

Faced with this, the integrated antenna 11 in the integrated detection module 1 cannot per se guarantee remote communication, because of intrinsic limitations due mainly to its small size. It should be noted that, in the embodiment described here, the electromagnetic circuit 2, thanks to the structure thereof, allows both telecommunications signals to be transmitted/received (for example, as already previously described, transmission of measured data and receiving of operating commands for the sensor), as well as an energy exchange to supply power (for example, as already previously described, receiving radio frequency waves to supply power).

In the embodiment shown in FIG. 1, the electromagnetic circuit 2 is in the form of an electromagnetic expansion and concentration device 2, having the property of concentrating an external electromagnetic field, and its related energy, on the integrated antenna 11 of the integrated detection module 1; and, similarly, of expanding an electromagnetic field emitted by the integrated antenna 11, and its related energy, towards a remote antenna, for example, of the external control and data collection system. Such an electromagnetic expansion and concentration device 2 comprises at least two antennas, for example, a first antenna 21 and a second antenna 22, connected together through an electrical connection network 23. Such an electric connection network 23 can, for example, be a simple transmission line or another circuit.

The first antenna 21 communicates with the integrated antenna 11 of the integrated detection module 1, by way of electromagnetic fields (symbolically indicated with F in FIG. 1), and in some embodiments through magnetic field coupling (i.e. near-field magnetic coupling). The second antenna 22 communicates with a remote antenna, for example, of the external control and data collection system, through coupling of electromagnetic fields (i.e. far-field electromagnetic coupling).

Figure 3:
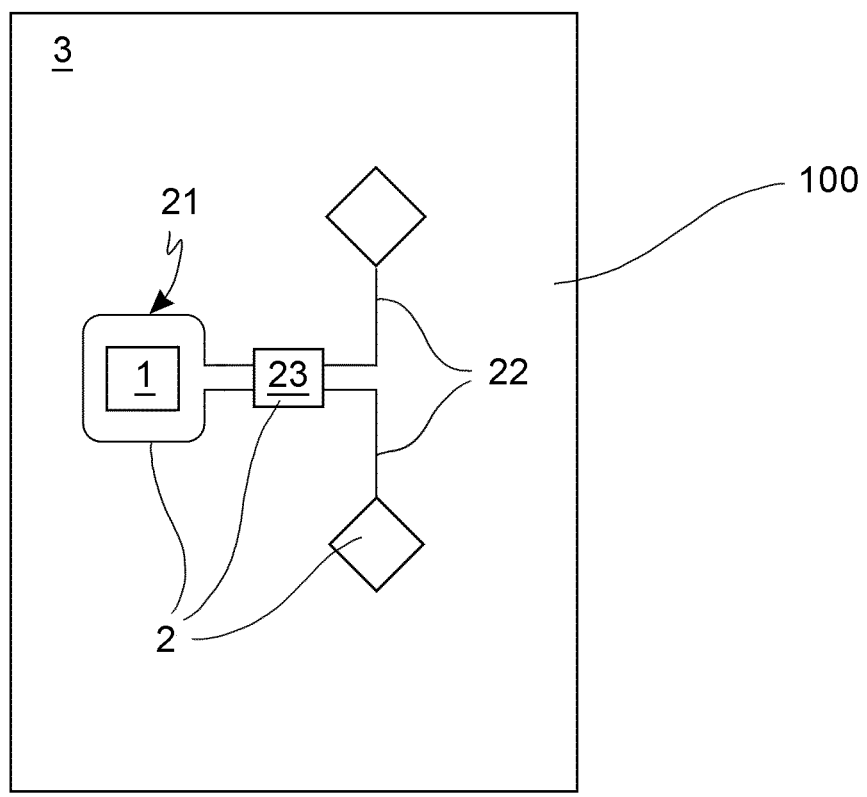
FIG. 3 is a schematic diagram of an electronic monitoring device, according to another embodiment of the present disclosure.

Each of the first and second antennas 21, 22 can be a magnetic dipole or a Hertzian dipole or even another type of known antenna, provided that it is able to perform the functions described above. Referring now to FIG. 3, a monitoring device 100 according to the present disclosure is shown from the structural point of view, and in particular, illustrating a further embodiment of the electromagnetic circuit 2.

It should be observed that in FIG. 3, the same numbering is used as in FIG. 1, where the parts indicated are the same or have the same function. In the embodiment shown in FIG. 3, the monitoring device 100 also comprises a support 3, for example, made from polymeric material, on which the integrated detection module 1 and the electromagnetic circuit 2 is positioned, for example, by gluing.

It should be noted that such a support 3 mainly performs the functions of keeping the integrated detection module 1 and the electromagnetic circuit 2 connected to one another, and also of keeping the monitoring device 100 in a predetermined position inside the structure to be monitored, as will be illustrated hereafter. In the embodiment illustrated in FIG. 3, the first antenna 21 of the electromagnetic expansion and concentration device 2 (i.e. of the electromagnetic circuit 2) comprises a coil 21. Moreover, the electrical connection network 23 of the electromagnetic expansion and concentration device 2 (i.e. of the electromagnetic circuit 2) comprises a typical adaptation circuit 23.

Furthermore, the second antenna 22 of the electromagnetic expansion and concentration device 2 (i.e. of the electromagnetic circuit 2) comprises a Hertzian dipole antenna 22. The coil 21 is placed close to the integrated detection module 1 and extends around it, so as to be magnetically coupled with the integrated antenna 11. The currents induced by the integrated antenna 11 on the coil 21, which acts as a magnetic dipole, are transferred to the Hertzian dipole antenna 22. Such a transfer is preferably mediated by the adaptation circuit 23, which allows the overall performance of the electromagnetic expansion and concentration device 2 to be improved.

As already observed, the second antenna 22 of the electromagnetic expansion and concentration device 2 is in this case a Hertzian dipole, suitable for far field communication. The electromagnetic circuit 2 can therefore be seen in this case as a hybrid transformer, in which a Hertzian dipole (i.e. the Hertzian dipole antenna 22) is magnetically coupled with the integrated antenna 11 of the integrated detection module 1.

Advantageously, the magnetic dipole, i.e. the coil 21, is designed so as to minimize its size and optimize its coupling with the integrated antenna 11. Also, the Hertzian dipole, i.e. the antenna 22, is designed so as to optimize far field communication. Regarding this, the size of the Hertzian dipole antenna is typically comparable to the operating wavelength, which is correlated to the communication frequency.

According to an embodiment, the monitoring device 100 according to the present disclosure can use the UHF transmission band, at frequencies around 800 MHz or over, which implies that it is equipped with a Hertzian dipole of reasonable size, of the order of centimeters. In other embodiments, other frequency bands may be used. It should be observed that a wide frequency band range can be used in different embodiments, finding a balance, according to the specific applications, between the communication distance to be guaranteed, on the one hand, and the size of the Hertzian dipole considered to be suitable, on the other.

From the point of view of the transmission bandwidth of the transmission/receiving channel associated with the monitoring device 100, there are no particularly strict requirements, since the type of communication that it must support is relatively simple and implies a small amount of information. A bandwidth of a few tens of KHz, for example, 200 KHz, is adequate.

As already observed, the electromagnetic circuit 2, on the basis of the same infrastructure already described, can not only transmit and receive telecommunications, but also receive energy from electromagnetic waves of adequate power, at frequencies within the working band of the Hertzian dipole antenna 22. Such received energy is used for the power supply (i.e., for the "remote power supply") of the integrated detection module 1, through the already described power supply circuit 12.

Figure 4:
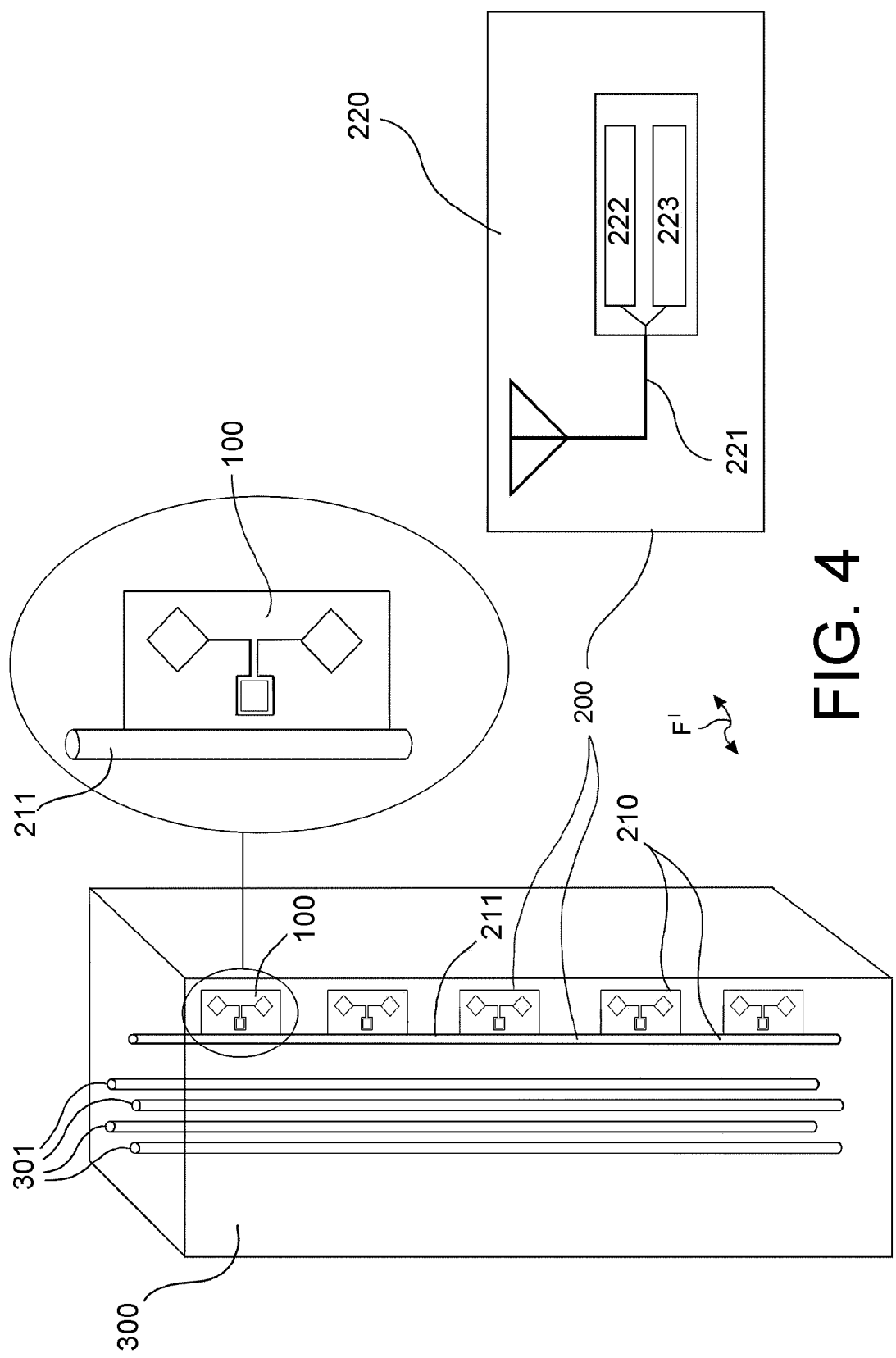
FIG. 4 is a schematic diagram showing a monitoring system, according to an embodiment of the present disclosure.

Referring now to FIG. 4, a system 200 for monitoring parameters within a solid structure (hereafter "monitoring system" 200), which exploits the monitoring device 100 described above. This monitoring system 200 is able to monitor one or more parameters in one or in a plurality of points (therefore "local" parameters) within a solid structure to be monitored. It should be noted that the representation of FIG. 4, being purely for illustrative purposes, is not to scale. In particular, the relative sizes of the monitoring devices 100 are enlarged in FIG. 4, for the sake of clarity.

The monitoring system 200, in the embodiment illustrated in FIG. 4, comprises an internal monitoring sub-system 210, inside (i.e. internal to) the solid structure 300, and an external control and data collection sub-system 220. It should be observed that in the example of FIG. 4, the structure to be monitored is a reinforced concrete pillar, comprising steel reinforcing rods 301. The internal monitoring sub-system 210 is therefore included within such a reinforced concrete pillar, already from when it is built. In particular, during construction, the internal monitoring sub-system 210 is suitably arranged in a desired position inside the volume determined by a formwork. Thereafter, liquid concrete is poured inside such a formwork, thus surrounding the internal monitoring sub-system 210 and, during solidification, traps it, so that such a sub-system is at the end "buried" inside the reinforced concrete pillar. Clearly, similar considerations also apply if the structure to be monitored structure is other than the above-mentioned pillar.

The internal monitoring sub-system 210 comprises a support structure of monitoring devices 211 (which we shall indicate hereafter as simply "support structure" 211) and a plurality of monitoring devices 100, according to the present disclosure, fixed to it. The support structure 211 is arranged to provide support and for fixing each monitoring device 100 of the plurality of monitoring devices 100, in the internal monitoring sub-system 210, in a known and predefined position. Such a support structure 211 extends inside the solid structure 300.

Figure 5:
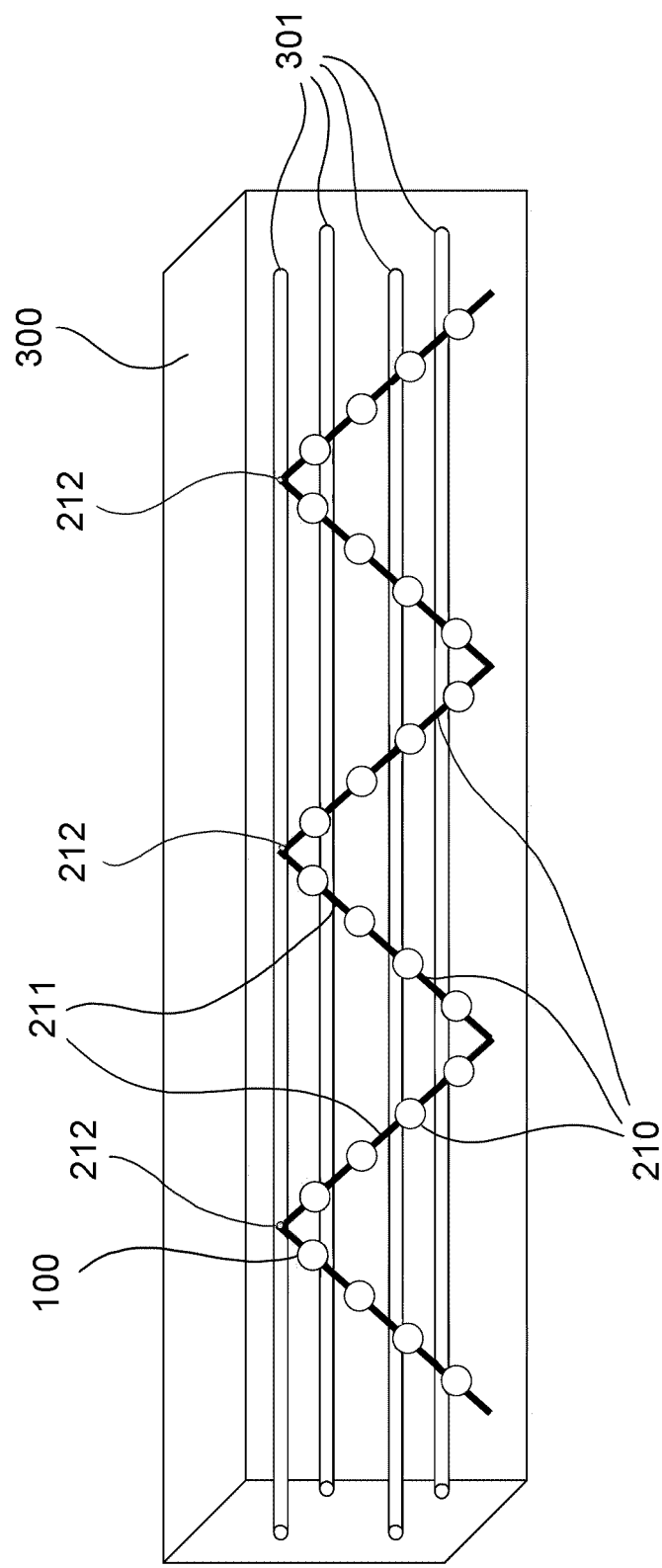
FIG. 5 shows an embodiment of an internal monitoring sub-system in the monitoring system, according to the present disclosure.

In the example of FIG. 4, the support structure 211 is a plumb-bob and it extends in a straight line along one dimension of the pillar 300. The positioning of the structure 211, in the example of FIG. 4, is along an axis parallel to the one of the reinforcement rods, but displaced with respect to them towards the peripheral part of the pillar, so that the reinforcement rods do not constitute an electromagnetic shield, deteriorating the electromagnetic communications from and towards the monitoring devices 100 supported by the support structure 211. In other embodiments, the support structure 211 can be of any shape, for example, straight along another dimension or else a polygonal chain (as shown in FIG. 5) or else semi-circular, or generically curvilinear, or other.

The criteria with which such a shape is set depend on the shape of the structure to be monitored: let us refer for example of a curvilinear shape, suitable for the curvilinear shape of the vault of a tunnel. The positioning of the support structure 211, in different embodiments, can be different from what has been illustrated in FIG. 4, provided that care is taken to ensure that the support structure 211 is positioned so that it is not shielded by the metallic structures possibly present in the solid structure 300 to be monitored.

It should be noted that the shape and positioning of the support structure 211 determine the geometric shape of the internal monitoring sub-system 210, which can be of many different types. The criteria with which the geometric shape of the internal monitoring sub-system 210 is determined, in the different embodiments, can depend on the shape of the structure to be monitored and on the selection of the significant points to be monitored within the structure itself (for example, along one or more axes of the structure, or in particularly critical points from the structural point of view).

The materials of which the support structure 211 is made can be various, for example, metallic or synthetic. A particular embodiment provides that the support structure 211 is a rope 211, pulled taut between anchoring points 212 to form whatever geometric shape, for example, a triangular wave (as illustrated in FIG. 5) or a square wave, or a spiral around reinforcement rods 301, or another irregular geometric shape. Such anchoring points 212 can, for example, be nails that partly penetrate the formwork in which the concrete casting takes place, during the construction of the structure to be monitored.

It should also be noted that the support structure 211, and therefore the geometric shape of the internal monitoring sub-system 210, can comprise different parts, not connected together, each of which having the characteristics listed above. One or a plurality of monitoring devices 100, according to the present disclosure, are connected to the support structure 211, by way of the support 3. Each of the monitoring devices 100 is fixed to the support structure 211 in a known and suitably predefined position. In particular, the support 3 can be glued or mechanically connected, in any typical way, to the support structure 211.

Figure 6A:
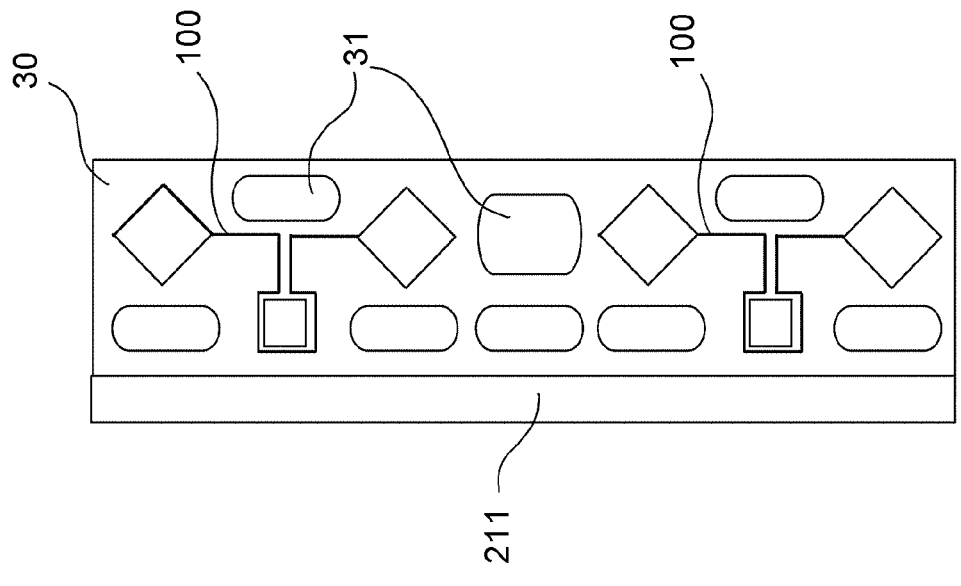
FIGS. 6A and 6B, respectively, are detailed diagrams showing two embodiments of an internal monitoring sub-system, according to the present disclosure.

According to an alternative embodiment, illustrated in FIG. 6A, there is a support strip 30 made from polymeric material, such as to be fixed to the support structure 211, and suitable for housing, at predefined distances and positions, a plurality of monitoring devices 100. The use of such a support strip 30, substituting a plurality of single supports 3, makes it possible to control the distance between the different monitoring devices 100 with greater precision.

Figure 6B:
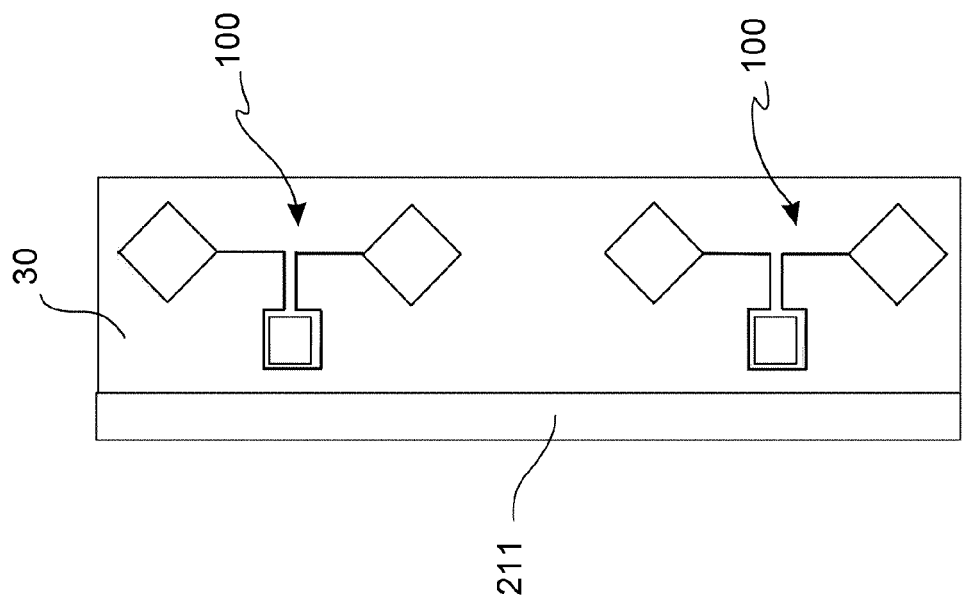

Advantageously, the support strip 30 can be perforated, having holes 31, as shown in FIG. 6B, so as to alter the structure to be monitored as little as possible. On a support strip 30, as illustrated in FIG. 7, there can be monitoring devices 100 having various types of electromagnetic expansion and concentration devices 2, which are different from one another. For example, there can be electromagnetic expansion and concentration devices for far field communication and electromagnetic expansion and concentration devices for near field communication.

Moreover, the electromagnetic expansion and concentration devices for far field communication can have different orientations, to take into account the different possible directions of arrival of the electromagnetic signals from the systems outside of (i.e., external to) the solid structure. Therefore, the antennas of such electromagnetic expansion and concentration devices can, for example, be antennas polarized in the vertical direction, antennas polarized in the horizontal direction and/or antennas oriented according to different angles according to the purposes.

Advantageously, embodiments are possible in which the same monitoring device comprises a plurality of integrated detection modules, and also comprises electromagnetic expansion and concentration devices having more than two antennas. For example, FIG. 7 illustrates a monitoring device 100' comprising two integrated detection modules 1' and 1", and an electromagnetic expansion and concentration device 2' having three antennas: one antenna 22' for far field communication; and two antennas 21', 21" for near field communication. The antennas 21' and 22' are suitable for communicating, respectively, with the two different integrated detection modules 1', 1", in the monitoring device 100'.

Again in FIG. 7, it can be seen how the antennas 21' and 21" for near field communication can be made, respectively, by means of a coil 21' and an additional coil 21", arranged in series with one another. The coil 21' is directly coupled with the antenna 22', whereas the additional coil 22" is coupled with the antenna 22' through the coil 21'. Such an approach can be advantageously applied in the case in which, in the same monitoring device, two integrated detection modules are used, one of which is redundant, so that the operation is not jeopardized if one of the two integrated detection modules is damaged, in which case the redundant integrated detection module will be used.

Such an approach can also be advantageously applied in the case in which the two integrated detection modules 1', 1" are two independent integrated detection modules, provided that provision is made to avoid interference between the communications related to the two modules. For example, for this purpose, it is possible to apply a communication protocol capable of avoiding the occurrence of interference between messages, as known, for example, in the RFID field; otherwise, it is possible to apply techniques for differentiating identification frequencies associated with the two different integrated detection modules 1', 1", as will be explained in detail hereafter.

Again with reference to the monitoring system 200 illustrated in FIG. 4, let us now consider the external control and data collection sub-system 220 (which is defined as the "external sub-system" 220). The external sub-system 220 comprises an external sub-system antenna 221 (which we shall define as "external antenna" 221), data collection, storage and processing means or circuit 222, power supplying and remote power supplying means or circuit 223. It should be noted that the external sub-system 220 can be advantageously situated in a suitable position that is convenient for installation, even at a certain distance from the structure to be monitored 300, provided that such a distance allows communication with the internal monitoring sub-system 210.

The external antenna 221, for this purpose, is able to communicate with each of the electromagnetic circuits 2 of each of the monitoring devices 100 in the internal monitoring sub-system 210, so as to exchange with it, as already illustrated, telecommunications and energy signals, through electromagnetic fields, indicated with F' in FIG. 4. In accordance with further embodiments, the external sub-system 220 can comprise any number of external antennas 221.

Through the external antenna 221, the external sub-system 220 receives the data, sent by one or by any plurality of devices 100 of the internal monitoring sub-system 210, representative of one or more parameters detected and measured by the respective sensors 10. The data thus received is forwarded to the data collection, storage and processing circuit 222.

Moreover, through the antenna 221, the external sub-system 220 sends control signals, for example, commands, to one or to any plurality of devices 100 of the internal monitoring sub-system 210. Such control signals are used, for example, to configure a given device 100, and/or to request the measurement of a certain parameter at a certain moment or continuously, or for other command, configuration or remote maintenance functions.

Finally, again through the antenna 221, the external sub-system 220 sends electromagnetic energy for remote power supplying of one or of any plurality of devices 100 of the internal monitoring sub-system 210. Such energy is supplied to the external antenna 221 by the power supplying and remote supplying circuit 223, for example, in the form of radio frequency waves, as already illustrated above.

Now with reference to the data collection, storage and processing circuit 222, it should be noted that it can be made by way of one or more processors, located physically together with the other elements of the external sub-system 220, or even placed remotely and connected together through any type of telecommunications network. Many different kinds of processing can be carried out by the data collection, storage and processing circuit 222, for example, and not for limiting purposes: monitoring of the spatial profile of different parameters, with or without interpolation; monitoring of the temporal and historical progression of different parameters; comparison with thresholds to determine possible conditions of degradation and of danger, and so on. With reference now to the power supplying and remote supplying circuit 223, it should be noted that it can include different types of power generators, based, for example, on solar cells, or on fuel cells, or on rechargeable batteries. An embodiment, in order to increase the autonomy time and minimize the maintenance of such power supplying and remote supplying circuit 223, comprises solar cells, for daylight operation, and one or more super-capacitors (for example, of 1 Farad 5 Volts, with dimensions 2×5 cm, thickness 3 mm), charged by the solar cells during the day, for night-time operation.

Taking a more detailed look at the telecommunication function (i.e. the remote communication mode) between the external sub-system 220 and the internal monitoring sub-system 210, the telecommunication function comprises an exchange of control signals and of signals relating to measured data, between the external sub-system 220 and each of the monitoring devices 100 of the internal sub-system 210. In order to manage such telecommunication, between many terminals and one collection point, known telecommunication protocols can be used, for example, protocols known in REID technology. For this purpose, each monitoring device 100 can be characterized by an individual code, programmed and written, for example, in a suitable memory element, such as an anti-fuse link or a fuse link or other.

Alternatively, according to an embodiment, with the individual code, it is possible to use an identifier frequency, assigned uniquely to each monitoring device 100. Such an identifier frequency, different and unique for each of the monitoring devices 100, allows "direct" communication to each monitoring device 100 over an individual physical channel. In this case, the electromagnetic circuit 2 of each monitoring device 100 will be able to transmit/receive signals at the respective identifier frequency. Advantageously, the use of an identifier frequency for each monitoring device 100 makes it possible to better manage the telecommunication between many terminals and a collection point, also allowing parallel, simultaneous communications.

It should be observed that the possibility of identifying the monitoring devices 100, according to any one of the ways indicated above, is very important not only for managing communications, but also to discriminate and suitably evaluate the data received, by the collection, storage and processing circuit 222. In particular, such collection, storage and processing circuit 222, by identifying a certain monitoring device 100, can also identify its position, which is known and predefined, in order to allow a simpler and more effective interpretation and processing of the data received. Moreover, in the case in which a monitoring device 100 were to malfunction or work incorrectly, the collection, storage and processing circuit 222 can recognize where the anomaly is, take into account the lack of data from a predetermined position, and obviate the anomaly, for example, by interpolating the data coming from devices adjacent to the one that is malfunctioning.

It should be noted that, in the monitoring device 100' embodiment illustrated in FIG. 7, it is advantageously possible to assign a different identifier frequency to each of the two integrated detection modules 1' and 1", so as to allow them to work independently, as already described above. As can be seen, the purpose of the present disclosure is accomplished by the monitoring device and by the monitoring system described above, by virtue of their characteristics. Indeed, the monitoring device of the present disclosure is simple, robust and reliable, capable of withstanding pressures and temperatures present inside a solid structure to be monitored, both during construction and during the respective operating lifetime, and also particularly robust with respect to the main causes of degradation, like those due for example to water and humidity. Moreover, the monitoring system of the present disclosure allows an effective exchange of information between a plurality of monitoring devices and an external data collection and processing sub-system, allowing the latter to individually recognize the monitoring devices, to know in a deterministic way their position and to correctly interpret their data.

A person skilled in the art can bring modifications, adaptations and replacements of elements with other functionally equivalent ones also in combination with the prior art, and even creating hybrid implementations, to the embodiments of the device and of the processing system described above, in order to satisfy contingent requirements, without departing from the scope of the following claims. Each of the characteristics described as belonging to a possible embodiment can be made independently from the other embodiments described.

The invention claimed is:

1. An electronic device for detecting and monitoring at least one local parameter within a solid structure, the electronic device comprising:
    an integrated detection module comprising a single IC chip, said integrated detection module comprising
        a functional integrated circuit (IC) comprising at least one sensor configured to detect the at least one local parameter within the solid structure, and an antenna, said functional IC having a functional circuitry surface facing towards an outside of the functional IC, and
        a passivation layer configured to cover at least said functional circuitry surface so that said integrated detection module is hermetically sealed and galvanically insulated from a surrounding environment; and
    a radiofrequency (RF) circuit separate from said integrated detection module and outside said passivation layer, said RF circuit configured to cooperate with said integrated detection module to transmit/receive signals for telecommunications and energy exchange between said antenna and a remote antenna via an electromagnetic coupling.

2. The electronic device of claim 1 wherein said passivation layer is configured to completely coat said single IC chip.

3. The electronic device of claim 1 wherein said at least one sensor is configured to detect the at least one parameter comprising at least one of a pressure parameter, a temperature parameter, and a mechanical stress parameter.

4. The electronic device of claim 3 wherein said at least one sensor comprises a pressure sensor configured to measure a pressure parameter based upon a piezo-resistance effect in silicon.

5. The electronic device of claim 3 wherein said at least one sensor comprises a temperature sensor configured to measure a temperature parameter based upon a temperature-dependent mobility variation in silicon.

6. The electronic device of claim 3 wherein said at least one sensor comprises a measurement circuit having a Wheatstone bridge configuration.

7. The electronic device of claim 6 wherein said at least one sensor comprises a first pair of resistors with a crystalline orientation using a piezoresistive effect, and a second pair of resistors with a crystalline orientation using piezoresistive effect so that the pressure parameter is measured independent from the temperature parameter.

8. The electronic device of claim 1 wherein said RF circuit comprises an electromagnetic expansion and concentration device comprising:
    a first antenna configured to communicate with said antenna via a magnetic coupling for near-field electromagnetic communication;
    a second antenna configured to communicate with the remote antenna of an external control and data collection system via a far-field electromagnetic communication; and
    an electric connection network configured to couple said first antenna and second antenna.

9. The electronic device of claim 1 further comprising an other integrated detection module, and an electromagnetic expansion and concentration device, said electromagnetic expansion and concentration device comprising:
    a first coil antenna configured to communicate with the antenna of said integrated detection module via magnetic coupling for near-field electromagnetic communication; and
    a second coil antenna configured to communicate with the antenna of the other integrated detection module via the magnetic coupling for near-field electromagnetic communication;
    said first coil antenna and other first coil antenna being coupled in series.

10. The electronic device of claim 1 wherein said integrated detection module comprises a driving circuit coupled to said antenna and configured to operate based upon radiofrequency identification (RFID) technology.

11. The electronic device of claim 1 wherein said antenna cooperates with said RF circuit and is configured to capture electromagnetic waves transmitted by the remote antenna for remote power supplying of the integrated detection module.

12. An electronic device for detecting and monitoring at least one local parameter within a solid structure, the electronic device comprising:
    an integrated detection module comprising
        a functional integrated circuit (IC) comprising at least one sensor configured to detect the at least one local parameter within the solid structure, and an antenna, said functional IC having a functional circuitry surface facing towards an outside of the functional IC, and
        a passivation layer configured to cover at least said functional circuitry surface; and
    a radiofrequency (RF) circuit separate from said integrated detection module and outside said passivation layer, said RF circuit configured to cooperate with said integrated detection module to transmit/receive signals for telecommunications and energy exchange between said antenna and a remote antenna via an electromagnetic coupling;

said passivation layer configured to seal said integrated detection module from a surrounding environment.

13. The electronic device of claim 12 wherein said passivation layer is configured to completely coat said functional IC so that said functional IC is hermetically sealed and galvanically insulated from a surrounding environment.

14. The electronic device of claim 12 wherein said at least one sensor is configured to detect the at least one parameter comprising at least one of a pressure parameter, a temperature parameter, and a mechanical stress parameter.

15. The electronic device of claim 14 wherein said at least one sensor comprises a pressure sensor configured to measure a pressure parameter based upon a piezo-resistance effect in silicon.

16. A system for monitoring at least one parameter in a plurality of points within a solid structure, the system comprising:

an internal monitoring system positioned in the solid structure and comprising
a support structure passing through the plurality of points to be monitored within the solid structure, and
a plurality of monitoring devices, each monitoring device being coupled to said support structure and comprising
an integrated detection module comprising a single IC chip, said integrated detection module comprising
a functional integrated circuit (IC) comprising at least one sensor configured to detect the at least one local parameter within the solid structure, and an antenna, said functional IC having a functional circuitry surface facing towards an outside of the functional IC, and
a passivation layer configured to cover at least said functional circuitry surface so that the integrated detection module is hermetically sealed and galvanically insulated from a surrounding environment, and
a radiofrequency (RF) circuit separate from said integrated detection module and outside said passivation layer, said RF circuit configured to cooperate with said integrated detection module; and
an external collection system positioned outside and remote with respect to the solid structure, said external collection system comprising
an external antenna configured to communicate with said RF circuit of said plurality of monitoring devices,
a data processing circuit configured to process data from said plurality of monitoring devices representative of the at least one parameter to be monitored, and
a power supply circuit configured to supply power to said external collection system and remotely supply power to said internal monitoring system via said external antenna.

17. The system of claim 16 wherein the solid structure to be monitored comprises a plurality of reinforcement structures; and wherein said support structure is positioned to reduce an electromagnetic effect due to said plurality of metallic reinforcement structures.

18. The system of claim 16 wherein each monitoring device is configured to operate at a unique identification frequency so that communication between each monitoring device and said external collection system occurs at a respective unique identification frequency of the respective monitoring device.

19. The system of claim 16 wherein said external collection system is configured to discriminate and interpret received data based upon a recognition of the respective monitoring device generating the received data, the recognition being based on the recognition of the unique identification frequency of the respective monitoring device.

20. The system of claim 16 wherein said passivation layer is configured to completely coat said single IC chip.

21. The system of claim 16 wherein said at least one sensor is configured to detect the at least one parameter comprising at least one of a pressure parameter, a temperature parameter, and a mechanical stress parameter.

22. A method for operating an electronic device to detect and monitor at least one local parameter within a solid structure, the electronic device comprising an integrated detection module comprising a single IC chip and including a functional integrated circuit (IC) comprising at least one sensor for detecting the at least one local parameter within the solid structure, and an antenna, the functional IC having a functional circuitry surface facing towards an outside of the functional IC, and a passivation layer covering at least the functional circuitry surface so that the integrated detection module is hermetically sealed and galvanically insulated from a surrounding environment, the method comprising:

operating a radiofrequency (RF) circuit to cooperate with the integrated detection module to transmit/receive signals for telecommunications and energy exchange between the antenna and a remote antenna via an electromagnetic coupling, the RF circuit being separate from the integrated detection module and outside the passivation layer.

23. The method of claim 22 wherein the passivation layer is configured to completely coat the single IC chip.

24. The method of claim 22 wherein the at least one sensor is configured to detect the at least one parameter comprising at least one of a pressure parameter, a temperature parameter, and a mechanical stress parameter.

25. A method for operating an electronic device to detect and monitor at least one local parameter within a solid structure, the electronic device comprising an integrated detection module including a functional integrated circuit (IC) comprising at least one sensor for detecting the at least one local parameter within the solid structure, and an antenna, the functional IC having a functional circuitry surface facing towards an outside of the functional IC, and a passivation layer covering at least the functional circuitry surface, the method comprising:

operating a radiofrequency (RF) circuit to cooperate with the integrated detection module to transmit/receive signals for telecommunications and energy exchange between the antenna and a remote antenna via an electromagnetic coupling, the RF circuit being separate from the integrated detection module and outside the passivation layer, the passivation layer configured to seal the integrated detection module from a surrounding environment.

26. The method of claim 25 wherein the passivation layer is configured to completely coat the functional IC so that the functional IC is hermetically sealed and galvanically insulated from a surrounding environment.

27. The method of claim 25 wherein the at least one sensor is configured to detect the at least one parameter comprising at least one of a pressure parameter, a temperature parameter, and a mechanical stress parameter.

* * * * *